United States Patent [19]

Dickinson et al.

[11] Patent Number: 5,207,224
[45] Date of Patent: May 4, 1993

[54] MAGNETIC RESONANCE APPARATUS

[75] Inventors: Robert J. Dickinson, Wealdstone; Christopher P. Randell, Uxbridge, both of England

[73] Assignee: Picker International, Ltd., Wembley, United Kingdom

[21] Appl. No.: 855,116

[22] Filed: Mar. 18, 1992

Related U.S. Application Data

[63] Continuation of Ser. No. 441,637, Nov. 27, 1989, abandoned.

[30] Foreign Application Priority Data

Dec. 9, 1988 [GB] United Kingdom ............... 8828810

[51] Int. Cl.⁵ ............................................. A61B 5/055
[52] U.S. Cl. ................................... 128/653.5; 324/318; 5/601
[58] Field of Search .......................... 128/653.2, 653.5; 324/309, 318, 322; 378/208, 209; 5/601, 600, 611

[56] References Cited

U.S. PATENT DOCUMENTS

| | | | |
|---|---|---|---|
| 4,681,308 | 7/1987 | Rice | 378/209 |
| 4,727,328 | 2/1988 | Carper et al. | 128/653.5 C |
| 4,771,785 | 9/1988 | Duer | 128/653.5 C |
| 4,777,464 | 10/1988 | Takabatashi et al. | 324/318 |
| 4,805,626 | 2/1989 | Di Massimo et al. | 128/653.5 C |
| 4,829,252 | 5/1989 | Kaufman | 324/318 |
| 4,862,086 | 3/1989 | Maeda | 324/318 |
| 4,875,485 | 10/1989 | Matsutania | 128/653.5 C |
| 4,960,106 | 10/1990 | Kubokawa et al. | 128/653.5 |

FOREIGN PATENT DOCUMENTS 0187389 7/1986 European Pat. Off. .

OTHER PUBLICATIONS

JP-A-61 114 148 (Sumitomo Special Metals Co., Ltd.) May 31, 1986.

Primary Examiner—Ruth S. Smith
Assistant Examiner—K. M. Pfaffle
Attorney, Agent, or Firm—Timothy B. Gurin

[57] ABSTRACT

A magnetic resonance imaging apparatus using a transverse magnet system (29) and having a patient handling arrangement (31, 33) which allows transport of a patient into the magnet system by first moving the patient in a direction (A) at right angles to the head-to-toe axis (B) of the patient. The patient's position in the magnet system may then be adjusted by movement in the head-to-toe axis direction. The area required to accommodate the apparatus is reduced compared with apparatus wherein patient transport is effected solely in the patient's head-to-toe axis direction.

13 Claims, 4 Drawing Sheets

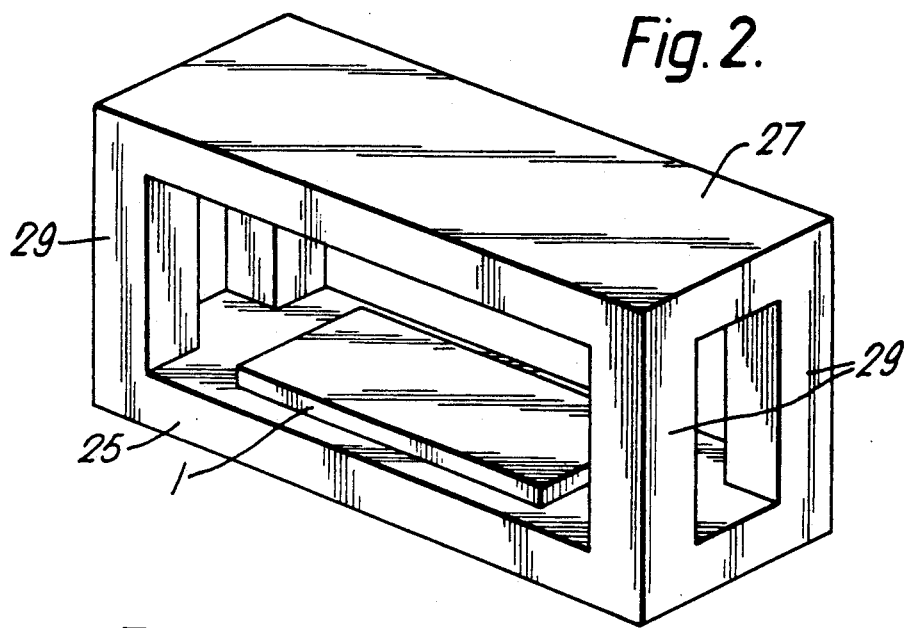
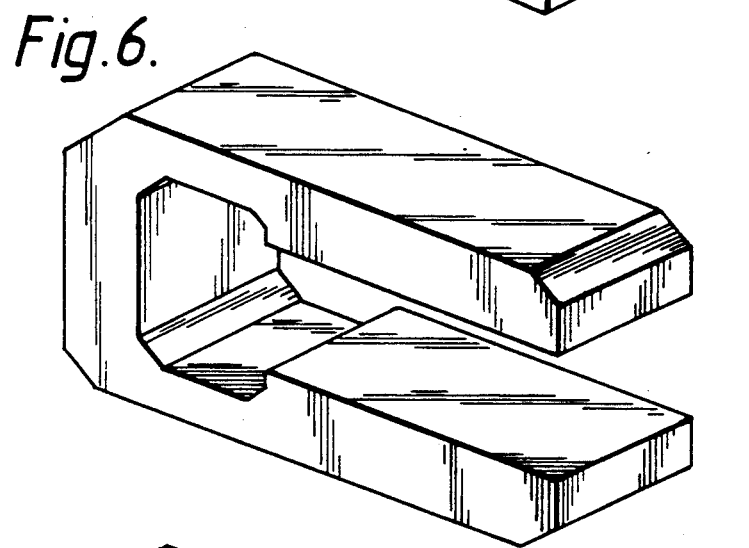
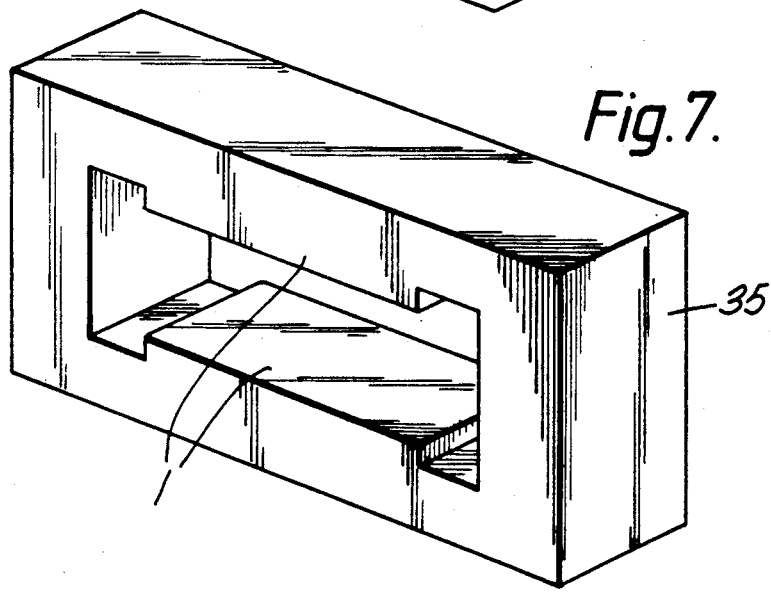

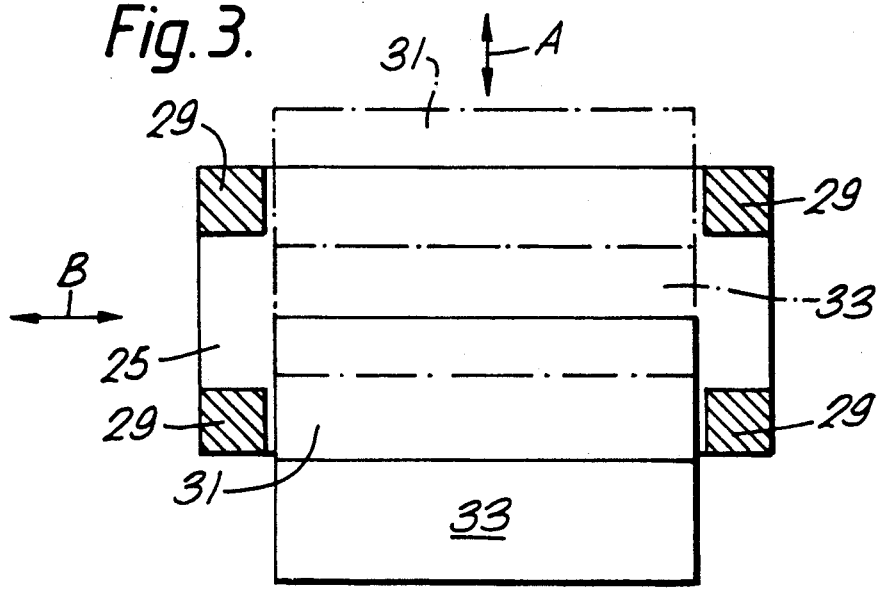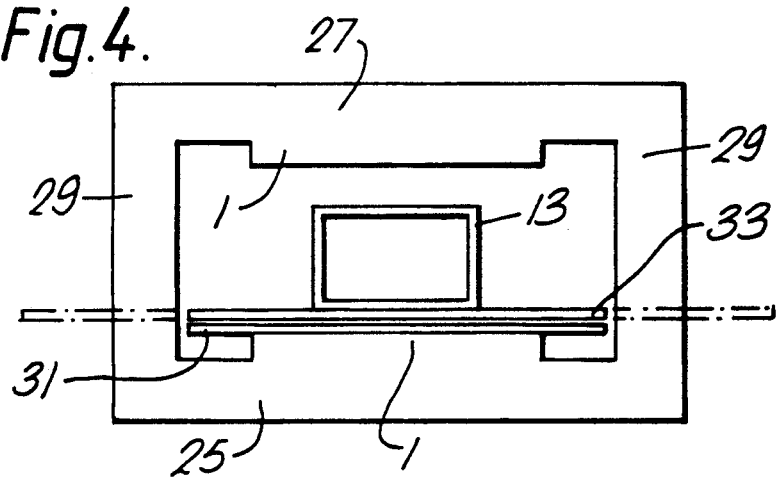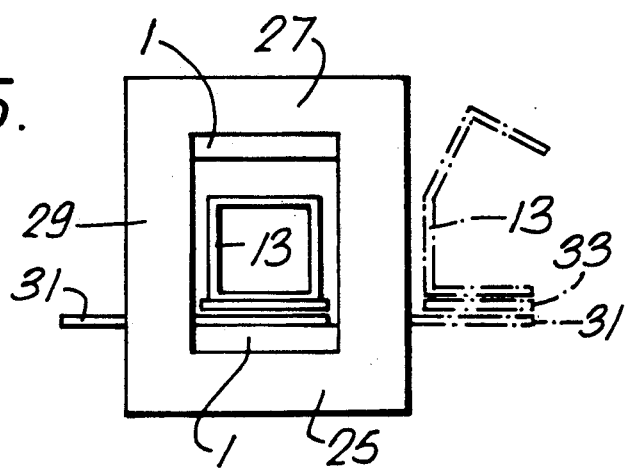

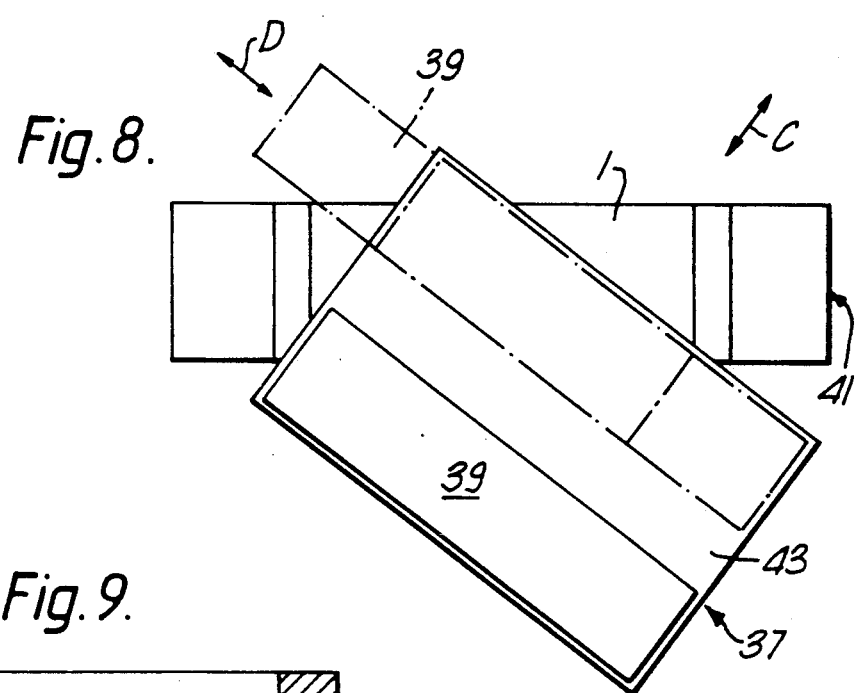
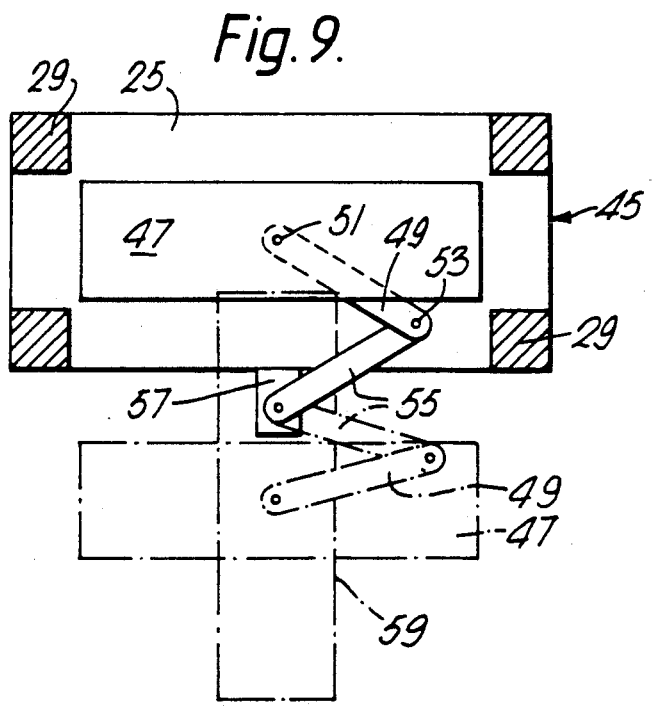
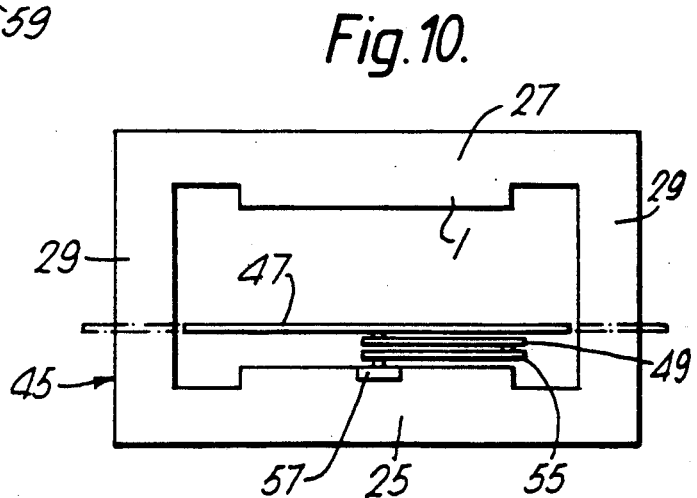

MAGNETIC RESONANCE APPARATUS

This is a continuation of copending application Ser. No. 07/441,637 filed on Nov. 27, 1989, now abandoned.

This invention relates to magnetic resonance (MR) apparatus.

MR apparatus includes, inter alia, a magnet system for producing a homogeneous static magnetic field of high strength in which the object to be examined, e.g. imaged, is positioned during examination, and which serves to define an equilibrium axis of magnetic alignment of nuclei within the object.

One particular application of MR apparatus is the examination of patients for medical diagnostic purposes. Such apparatus is often designed so as to be capable of examining any desired part of the whole body of a patient. The magnet system of such a so-called "whole body" MR apparatus is necessarily quite bulky and where, as is normally the case, the patient is inserted into the apparatus whilst lying horizontally in the direction of the head-to-toe axis of the patient, the MR apparatus together with the associated patient handling equipment requires a large floor area to accommodate it, i.e. has a large so-called "footprint".

It is an object of the present invention to provide an MR apparatus wherein this problem is alleviated.

According to the present invention there is provided an MR apparatus including a magnet system including a magnetic core arrangement which is shaped so as to provide in a gap between a pair of opposed surfaces of the core arrangement a static magnetic field for defining an equilibrium axis of magnetic alignment of nuclei within an object under examination; and an object handling equipment including an object support member of elongated form adapted to support an object for examination and capable of translational movement in a plane transverse to the direction of the magnetic field in said gap in a direction transverse to the longitudinal axis of said support member, the extent of said movement being sufficient to allow an object on said support member to be moved between a position within said gap and a position substantially wholly outside said gap.

Typically said plane is orthogonal to said magnetic field direction.

Preferably said support member is further capable of translational movement in said plane in a second direction at an angle to the first-mentioned direction of translational movement at least when said support member is at a position such that said object is within said gap.

Preferably said first-mentioned and second directions are respectively orthogonal to and parallel to said longitudinal axis.

In one particular embodiment of the invention said support member is capable only of translational movement in said plane.

In another particular embodiment of the invention said support member is also capable of rotational movement about axes normal to said plane.

Where the apparatus is a whole body MR apparatus for examining patients, said support member is suitably adapted to support a patient whilst lying horizontally with the head-to-toe axis of the patient parallel to said longitudinal axis of the support member.

Several MR apparatuses in accordance with the invention will now be described, by way of example, with reference to the accompanying drawings in which:

FIG. 2 is a diagram illustrating a magnetic core arrangement of a magnet system of a first apparatus according to the invention;

FIGS. 3, 4 and 5 are respectively diagrammatic plan, side and end views of the magnetic core arrangement and a patient handling equipment of the first apparatus;

FIG. 6 is a diagram illustrating an alternative form for the magnetic core arrangement of the first apparatus;

FIG. 7 is a diagram illustrating a magnetic core arrangement of a second apparatus in accordance with the invention;

FIG. 8 is a diagrammatic plan view of the magnetic core arrangement and a patient handling system of the second apparatus; and FIGS. 9 and 10 are respectively diagrammatic plan and side views of a magnetic core arrangement and patient handling equipment of a third apparatus according to the invention.

Figure 1:
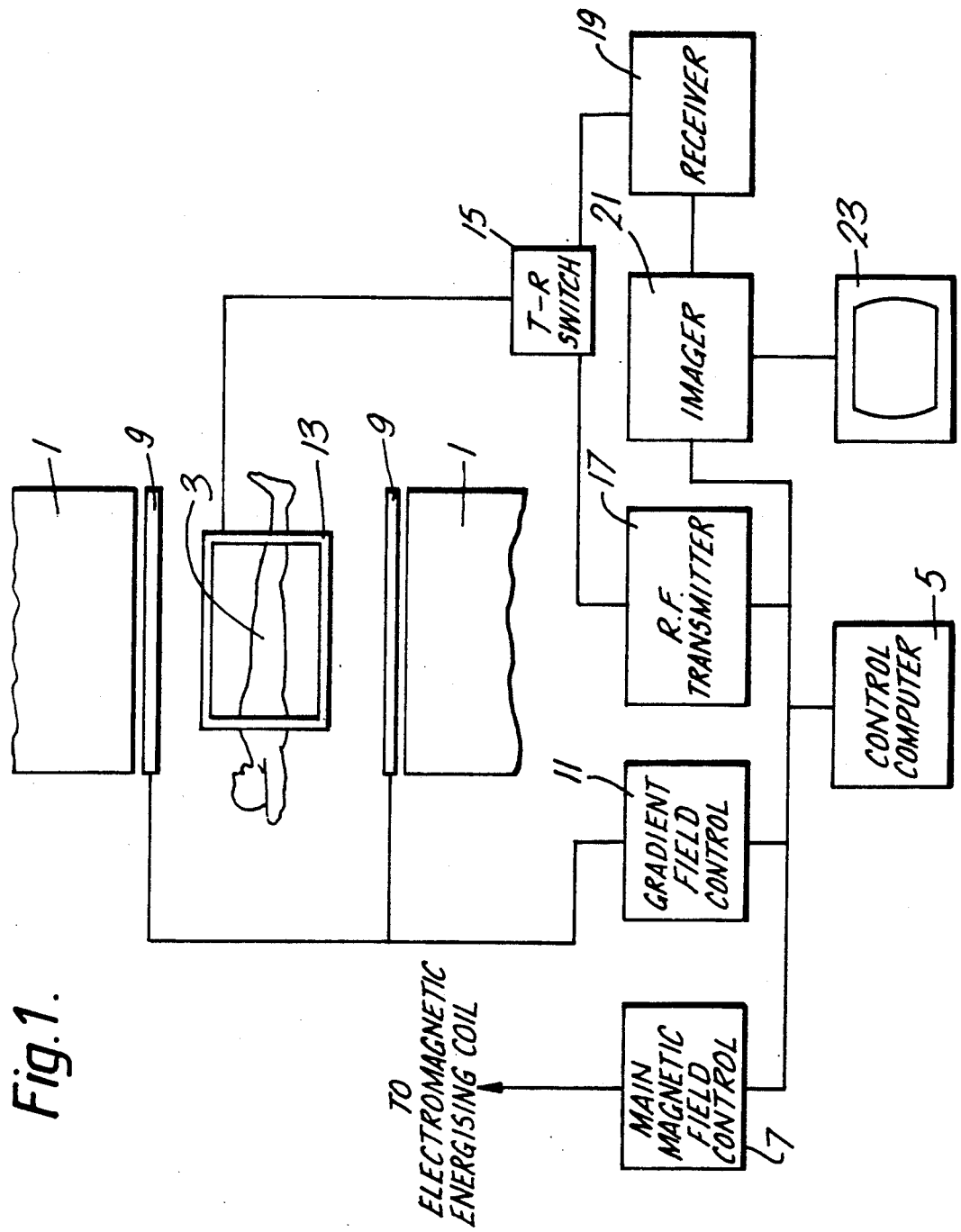
FIG. 1 is a schematic diagram showing the general arrangement of all the apparatuses to be described.

Referring to FIG. 1, the apparatuses, which are diagnostic patient imaging apparatuses, include an electromagnet which produces a strong uniform static main magnetic field Bo across a gap between two pole pieces 1 of a magnetic core arrangement of the electromagnet, the pole pieces 1 being joined by a yoke (not shown in FIG. 1) carrying an energising coil (not shown). In use of the apparatus a patient 3 to be imaged is placed in the gap between the pole pieces lying horizontally on a support member of a patient handling equipment (not shown) so that the head-to-toe axis of the patient 3 is orthogonal to the direction of the magnetic field in the gap. The strength of the field in the gap between the pole pieces 1, and hence in the patient's body, is controlled by a computer 5 via a main magnet control means 7 which controls the supply of energising current to the electromagnet energising coil.

The apparatus further includes a gradient coil system 9 whereby a gradient may be imposed on the static magnetic field in the gap between the pole pieces 1 in any one or more of three orthogonal directions. The coil system 9 is energised by a gradient field control means 11 under control of the computer 5.

The apparatus further includes an r.f. antenna system 13.

The antenna system 13 is selectively connectable by way of a transmit-receive switch 15 either to an r.f. transmitter 17 or a receiver 19. The transmitter 17 is operated under control of the computer 5 to apply r.f. field pulses to the patient's body 3 for excitation of magnetic resonance in the patient's body 3. R.f. signals resulting from magnetic resonance excited in the body are sensed by the antenna system 13 and passed via the receiver 19 to an imager 21 which under control of the computer 5 processes the signals to produce signals representing an image of the body 3. These signals are, in turn, passed to a display device 23 to provide a visual display of the image.

In operation of the apparatus the field provided by the electromagnet defines an equilibrium axis of magnetic alignment in the body 3.

To obtain an image of a selected region, e.g. a cross-sectional slice of the patient's body 3, an r.f. field pulse is first applied to the body 3 by means of the r.f. transmitter 17 and antenna system 13 to excite magnetic resonance in the selected region. To this end the antenna system 13 produces a field B1 in a direction orthogonal to the static field direction so as to tip the spins of nuclei in the selected region from the direction of the static field into a plane orthogonal to the static field direction. To restrict excitation to the selected region the r.f. field pulse is applied in conjunction with magnetic field gradients imposed by the coil system 9, the frequency of the r.f. field being chosen in conjunction with the magnitudes and directions of the imposed gradients so that the Larmor frequency of chosen protons in the body, e.g. hydrogen protons, is equal to the r.f. field frequency only in the selected region.

The r.f. signals resulting from excitation are then spatially encoded by application of one or more further gradient magnetic fields in known manner, detected by the antenna system 13 and processed to produce an image.

Normally a number of excitation and signal detection sequences are required to produce sufficient data to produce a satisfactory image.

Instead of using a T-R switch, the antenna system 13 may comprise separate transmitting and receiving coil arrangements respectively connected with transmitter 17 and receiver 19.

In one embodiment of the apparatus of FIG. 1 in accordance with the present invention, the electromagnet is of the so-called four-poster bed type, i.e. the magnetic core arrangement of the electromagnet is similar in shape to a four-poster bed, as shown in FIG. 2. Thus the yoke joining the pole pieces 1 comprises horizontal spaced apart planar rectangular base and roof portions 25 and 27 joined by vertical posts 29, one at each corner, with the pole pieces 1 extending towards one another from the centre of the base and roof portions 25 and 27 respectively.

Referring to FIGS. 3, 4 and 5, the patient handling equipment of this embodiment comprises a lower horizontal rectangular planar table portion 31 mounted with its longer axis parallel to the longer horizontal axis of the magnetic core arrangement on rails or rollers (not shown), just above the face of the lower pole piece 1, so as to be slidable in a horizontal plane in a direction orthogonal to the longer axis of the core arrangement. On its upper surface adjacent a longer side the table portion 31 carries an elongated rectangular patient support member or platter 33 arranged to be slidable on the table portion 31, e.g. on rails or rollers, in the direction of its longer axis, which axis is parallel to the longer axis of the table portion 31.

The patient platter 33 is thus capable of translational movement in two directions in a plane orthogonal to the direction of the magnetic field in the gap between the pole pieces 1, the two directions being respectively orthogonal and parallel to the longer axis of the platter 33, as indicated by arrows A and B in FIG. 3.

In use of the apparatus the table portion 31 is slid out from the core arrangement from the side at which the platter 33 is mounted so as to move the platter 33 in the direction of arrow A orthogonal to its longer axis to a position in which it is wholly outside the core arrangement, as shown in full lines in FIG. 3. The patient is then placed on the platter 33 and the table portion 31 slid back into the core arrangement to bring the platter 33, and hence the patient's body, to a position where it extends centrally through the gap between the pole pieces, as shown in chain-dotted lines in FIG. 3. The platter 33 can then be slid along the table portion 31 in the direction of arrow B, i.e. the direction of its longer axis, to bring the particular section of the patient's body it is desired to image to a position centrally between the pole pieces 1, if necessary passing between the closer spaced pairs of the posts 29, as shown in chain-dotted lines in FIG. 4.

The r.f. antenna system 13 is suitably carried on the patient platter 33 and where, as is normally the case, it is required to surround the patient's body, it may be of a hinged construction to allow side access to the platter 33, as illustrated in dotted lines in FIG. 5.

It will be appreciated that the form of patient handling equipment illustrated in FIGS. 3, 4 and 5 is also suitable for use with magnetic core arrangement of C-shape, as illustrated in FIG. 6.

Where the magnetic core arrangement is of so-called H-form, as illustrated in FIG. 7, i.e the pole pieces 1 are joined by a yoke 35 of planar rectangular form with the pole pieces 1 positioned centrally on opposite limbs of the yoke 35, a patient handling equipment 37 of similar form to that illustrated in FIGS. 3 to 5 may be used. However, in this case the longer axis of the patient support platter 39 is at an acute angle to the longer axis of the core arrangement 41, as illustrated in FIG. 8, and the patient platter 39 is slidable in two orthogonal directions, indicated by arrows C and D, on a lower table 43 which is fixed with respect to the magnet core arrangement 41. The platter 39 when slid into a position adjacent the gap between the pole pieces 1 by movement in direction C orthogonal to its longer axis is then able to be slid in direction D so as to pass diagonally through the core arrangement 41 via the gap between the pole pieces 1.

In further embodiments of the invention, suitable for use with magnetic core arrangements of any of the above-described forms, the patient-handling equipment comprises a patient support member arranged for rotational motion as well as translational motion.

One such embodiment is illustrated in FIGS. 9 and 10 wherein a four-poster bed magnetic core arrangement 45 is shown by way of example. In the embodiment of FIGS. 9 and 10 the patient handling equipment comprises a horizontal planar rectangular patient support member 47 which at a central position on its underside is mounted on one end of a horizontal arm 49 for pivotal movement about a vertical axis 51. At its other end the arm 49 is, in turn, mounted for pivotal motion about a vertical axis 53 at one end of a second horizontal arm 55 whose other end is similarly pivotally connected to a flange member 57 fixed with respect to the core arrangement 45.

The support member 47 is thus capable of translational motion, with its longer axis parallel to the longer horizontal axis of the core arrangement 45, in directions orthogonal and parallel to its own longer axis, as indicated by chain-dotted lines in FIGS. 9 and 10, in exactly the same manner as the platter 33 of FIGS. 3 to 5. In addition, the support member 47 is capable of rotational movement in a horizontal plane at any position reached by the translational movement.

Such an arrangement exhibits several advantages. For example, if space permits, when the patient is removed from the core arrangement, the member 47 may be rotated through 90° to the position indicated by dotted line 59 in FIG. 9 to permit access to both sides of a patient. In addition, positioning of the patient's head-to-toe axis other than parallel to the longer axis of the core arrangement 45 is possible, and the direction of the patient's head-to-toe axis may be reversed without removing the patient from the support member 47. The latter feature may be of particular benefit if the available space severely limits movement of the support member 47 in the direction of the longer axis of the core arrangement 45.

It will be appreciated that the apparatus described above by way of example with reference to FIGS. 3 to 5 and FIG. 8 may easily be modified to permit rotational movement of the support members 33 and 39.

We claim:

1. A whole body magnetic resonance apparatus including a magnet system comprising a magnetic core arrangement having a pair of spaced apart and opposed planar surfaces separated by at least one magnetically susceptible yoke defining an established gap therebetween; means for producing a static magnetic field between said surfaces and in a direction across said gap; said field defining an equilibrium axis of magnetic alignment of nuclei within an object placed in the gap for examination in the apparatus; means for superimposing a gradient magnetic field on said static magnetic field in at least one of three orthogonal directions; means for applying a radio frequency field to said object in said gap; means for detecting a radio frequency field emanating from said object in said gap; means for controlling said static, gradient and applied radio frequency fields in said gap; and an object handling equipment including an object support member of elongated form adapted to support the object for examination and translating means for providing translational movement of the support member into and out of said gap in a plane transverse to the magnetic field direction and in a first direction transverse to the longitudinal axis of said support member, and of an extent sufficient to allow the object on said support member to be moved between a position within said gap and a position wholly outside of said gap such as to avoid interference between the object and the magnetic core arrangement as the object is placed on and removed from said support member.

2. An apparatus according to claim 1 wherein said plane is orthogonal to said magnetic field direction.

3. An apparatus according to claim 1 wherein said translating means comprises means permitting only translational movement in said plane.

4. An apparatus according to claim 1 wherein the examined object is a patient and wherein said support member comprises means arranged to support the patient so that the patient lies horizontally with the head-to-toe axis of the patient parallel to said longitudinal axis of the support member.

5. A magnetic resonance apparatus including a magnet system comprising a magnetic core arrangement having a pair of opposed surfaces with a gap therebetween; and means for producing a magnetic field in said gap; said field defining an equilibrium axis of magnetic alignment of nuclei within an object placed in the gap for examination in the apparatus; means for superimposing a gradient magnetic field on said static magnetic field in at least one of three orthogonal directions; means for applying a radio frequency field to said object in said gap; means for detecting a radio frequency field in the object in said gap; means for controlling said static, gradient and radio frequency fields in said gap; and an object handling equipment including an object support member of elongated form adapted to support an object for examination and translating mean for providing translational movement of the support member into and out of said gap in a plane transverse to the magnetic field direction and in a first direction transverse to the longitudinal axis of said support member, and of an extent sufficient to allow an object on said support member to be moved between a position within said gap and a position wholly outside of said gap such as to avoid interference between the object and the magnetic core arrangement as the object is placed on and removed from said support member; and wherein said translating means also permits translational movement of the support member in said plane in a second direction at any angle to the first direction transverse to the longitudinal axis of said support member at least when said support member is at a position such that said object is within said gap.

6. An apparatus according to claim 5 further including an underlying member on which said support member is mounted slidably by said translating means for translational movement of said support member with respect to said underlying member in said second direction, and said underlying member is slidably mounted with respect to said core arrangement for movement of said support member in said first direction.

7. An apparatus according to claim 5 further including an underlying member on which said support member is mounted slidably by said translating means for translational movement of said support member with respect to said underlying member both in said first direction and in said second direction.

8. An apparatus according to claim 5 wherein said first and second directions are respectively orthogonal to and parallel to said longitudinal axis.

9. An apparatus according to claim 8 wherein said core arrangement is of rectangular cross-section in planes orthogonal to the direction of said magnetic field and the longer sides of said cross-section are substantially orthogonal to said first direction.

10. An apparatus according to claim 9 further including an underlying member on which said support member is mounted slidably by said translating means for translational movement of said support member with respect to said underlying member in said second direction, and said underlying member is slidably mounted with respect to said core arrangement for movement of said support member in said first direction, and wherein said core arrangement is a four-poster bed core arrangement; said underlying member being arranged to pass between the pair of posts of the core arrangement at opposite ends of the longer side of the core arrangement when slid in said first direction; and said support member being arranged to pass between the pairs of posts of the core arrangement at opposite ends of the shorter sides of the core arrangement when slid in said second direction.

11. An apparatus according to claim 5 further including an underlying member on which said support member is mounted slidably by said translating means for translational movement of said support member with respect to said underlying member both in said first direction and in said second direction; wherein said core arrangement comprises a yoke portion of planar rectangular form having a pair of opposite limbs with said opposed surfaces respectively positioned centrally along said limbs; and said support member is disposed with its longitudinal axis at an acute angle to the lengths of said opposite limbs so as to be capable of passing diagonally through said core arrangement via said gap when undergoing said translational movement in said second direction when in at least one position along said first direction.

12. A magnetic resonance apparatus including a magnet system comprising a magnetic core arrangement having a pair of opposed surfaces with a gap therebetween; and means for producing a magnetic field in said gap; said field defining an equilibrium axis of magnetic alignment of nuclei within an object placed in the gap for examination in the apparatus; means for superimposing a gradient magnetic field on said static magnetic field in at least one of three orthogonal directions; means for applying a radio frequency field to said object in said gap; means for detecting a radio frequency field in the object in said gap; means for controlling said static, gradient and radio frequency fields in said gap; and an object handling equipment including an object support member of elongated form adapted to support an object for examination and translating means for providing translational movement of the support member into and out of said gap in a plane transverse to the magnetic field direction and in a first direction transverse to the longitudinal axis of said support member, and of an extent sufficient to allow an object on said support member to be moved between a position within said gap and a position wholly outside of said gap such as to avoid interference between the object and the magnetic core arrangement as the object is placed on and removed from said support member; including rotating means whereby said support member is also capable of rotational movement about axes normal to said plane.

13. An apparatus according to claim 12 wherein said rotating means includes a first arm and a second arm wherein the support member is pivotally mounted for rotation in said plane at one end of said first arm whose other end is pivotally mounted to one end of said second arm which at its other end is pivotally mounted for rotation about an axis fixed with respect to said core arrangement.

* * * * *